US00PP08189P

United States Patent [19]

Zaiger et al.

[11] Patent Number: Plant 8,189

[45] Date of Patent: Mar. 30, 1993

[54] AUTUMN BEAUT

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95351

[21] Appl. No.: 829,225

[22] Filed: Feb. 3, 1992

[51] Int. Cl.[5] ..... A01H 5/00

[52] U.S. Cl. ..... Plt./38.1

[58] Field of Search ..... Plt./38.1

*Primary Examiner*—James R. Feyrer

[57] ABSTRACT

A new and distinct variety of plum tree which has the following unique combination of desirable features that are outstanding in a new variety:

1. Late maturity of fruit.
2. Regular and heavy bearing of large size fruit.
3. Fruit holding firm on the tree 10 to 14 days after picking ripe.
4. Relatively uniform ripening of fruit throughout the tree.
5. Fruit with good flavor and eating quality.
6. Fruit having very good storage and shipping quality.

1 Drawing Sheet

ORIGIN OF THE VARIETY

The present new variety of plum tree was originated by us in our experimental orchard, located near Modesto, Calif. as a first generation cross between a selected seedling originating from open pollinated Roysum Plum (U.S. Plant Pat. No. 2,619) seeds and Eldorado Plum (Non-patented). A large number of these first generation seedlings were grown under careful observation by us, one such late maturing seedling having been especially desirable with respect to its fruit was selected for asexual reproduction and commercialization.

ASEXUAL REPRODUCTION OF THE VARIETY

Asexual reproduction by budding of the new and distinct variety of plum tree was performed by us in our experimental orchard located near Modesto, Calif. and shows that all characteristics run true to the original tree and are established and transmitted through succeeding propagations.

SUMMARY OF THE NEW VARIETY

A new and distinct variety of plum tree which is of large size, vigorous, upright in growth and a productive and regular bearer of large, firm, clingstone fruit having brownish maroon to blackish blue skin color. The fruit is further characterized by having good flavor and eating quality, having very good storage and shipping quality and being late in maturity; in comparison to Roysum Plum (U.S. Plant Pat. No. 2,619) the fruit ripens 6 days earlier and is not susceptible to skin cracking or preharvest drop of immature fruit.

DESCRIPTION OF THE PHOTOGRAPHS

The accompanying color photographic reproductions show the foliage and fruit of the present new variety with the upper and lower surface of the leaves being shown, an exterior and cross sectional view of the fruit divided in the suture plane to reveal flesh coloration, pit cavity and a stone remaining in place. The photographic illustrations were taken shortly after being picked at maturity (firm ripe) and the colors are as nearly true as is reasonably possible in a color representation of this type.

DESCRIPTION OF THE VARIETY

The botanical detailed description of the present new and distinct variety of plum tree, its foliage, flowers and fruit are based on observations of specimens grown near Modesto, Calif., with color terminology (except those in common terms) referenced to Reinhold Color Atlas by A. Kornerup and J. H. Wanscher.

Tree:
- *Size.*—Large.
- *Vigor.*—Vigorous.
- *Form.*—Upright.
- *Density.*—Medium dense.
- *Production.*—Productive.
- *Bearer.*—Regular.

Trunk:
- *Size.*—Medium to large.
- *Texture.*—Medium rough.
- *Color.*—Brown to grayish brown (7-E-3) to (7-E-4).

Branches:
- *Size.*—Medium.
- *Angles.*—Moderately narrow.
- *Texture.*—Medium shaggy.
- *Lenticels.*—Medium size. Numerous.
- *Color.*—Brown to reddish brown (8-E-4) to (8-E-5).

Leaves:
- *Size.*—Medium. Average length — 4". Average width — $1\frac{7}{8}$".
- *Texture.*—Smooth.
- *Margin.*—Finely serrate.
- *Petiole.*—Medium length. Medium thickness.
- *Shape.*—Lanceolate.
- *Glands.*—Globose. Number varies 0 to 4. Average number 2. Located on upper portion of petiole and base of leaf blade.
- *Color.*—Upper surface — green to dark green (27-E-7) to (27-F-7). Lower surface — dull green to green (27-D-5) to (27-D-6).

Flower buds:

*Size.*—Small to medium.
*Length.*—Medium.

Flowers:
*Size.*—Small to medium.
*Blooming period.*—Mar. 1, 1989 to Mar. 10, 1989. Varies slightly due to weather conditions.
*Pollen.*—Viable pollen is produced, but incompatible with pistils.
*Color.*—White.

Fruit:
*Maturity when described.*—Firm ripe.
*Date of first picking.*—Sep. 10, 1989.
*Date of last picking.*—Sep. 16, 1989.
*Size.*—Large. Average diameter axially — 2⅜". Average transversely in suture plane — 2½". At right angles to suture plane — 2½".
*Form.*—Globose. Nearly symmetrical.
*Suture.*—Shallow — extends from base to slightly passed apex on most fruit.
*Ventral surface.*—Nearly rounded — very slightly lipped.
*Cavity.*—Rounded to elongated in suture plane. Average depth — ⅜". Average breadth — ½".
*Base.*—Retuse.
*Apex.*—Rounded to slightly retuse in suture plane.

Skin:
*Thickness.*—Medium.
*Texture.*—Medium — tenacious to flesh.
*Down.*—Wanting.
*Tendency to crack.*—None.
*Color.*—Brownish maroon (11-F-8) to blackish blue (19-F-4).

Flesh:
*Texture.*—Firm, meaty.
*Ripens.*—Evenly.
*Flavor.*—Mild — good balance between acid and sugar.
*Aroma.*—Very slight.
*Eating quality.*—Good.
*Color.*—Light yellow (3-A-4). Lighter yellowish white streaks (1-A-2) extending out from pit cavity toward skin surface. Surface of pit cavity — brownish orange (4-C-5).

Stone:
*Size.*—Medium. Average length — 1 1/16". Average width — ⅝". Average thickness — 5/16".
*Form.*—Ovoid.
*Type.*—Clingstone.
*Sides.*—Mostly equal — some unequal.
*Base.*—Varies from straight to rounded.
*Apex.*—Cuspidate.
*Surface.*—Only slightly furrowed near apex. Pitted throughout, heavier near base.
*Tendency to split.*—None.
*Color.*—Light brown to brown (7-D-4) to (7-D-5).

Storage quality: Very good.
Shipping quality: Very good.

The new and distinct variety of plum tree, its foliage and fruit herein described may vary in slight detail due to climatic, soil conditions and cultural practices under which the variety may be grown; the present description is that of the variety grown under the ecological conditions prevailing near Modesto, Calif.

The following is claimed:

1. A new and distinct variety of plum tree, substantially as illustrated and described, characterized by its large size, vigorous, upright growth and a productive and regular bearer of large size, firm, late maturing, clingstone fruit and in comparison to the late maturing Roysum Plum (U.S. Plant Pat. No. 2,619) the fruit ripens approximately 6 days earlier, is not susceptible to skin cracking or preharvest drop of immature fruit.

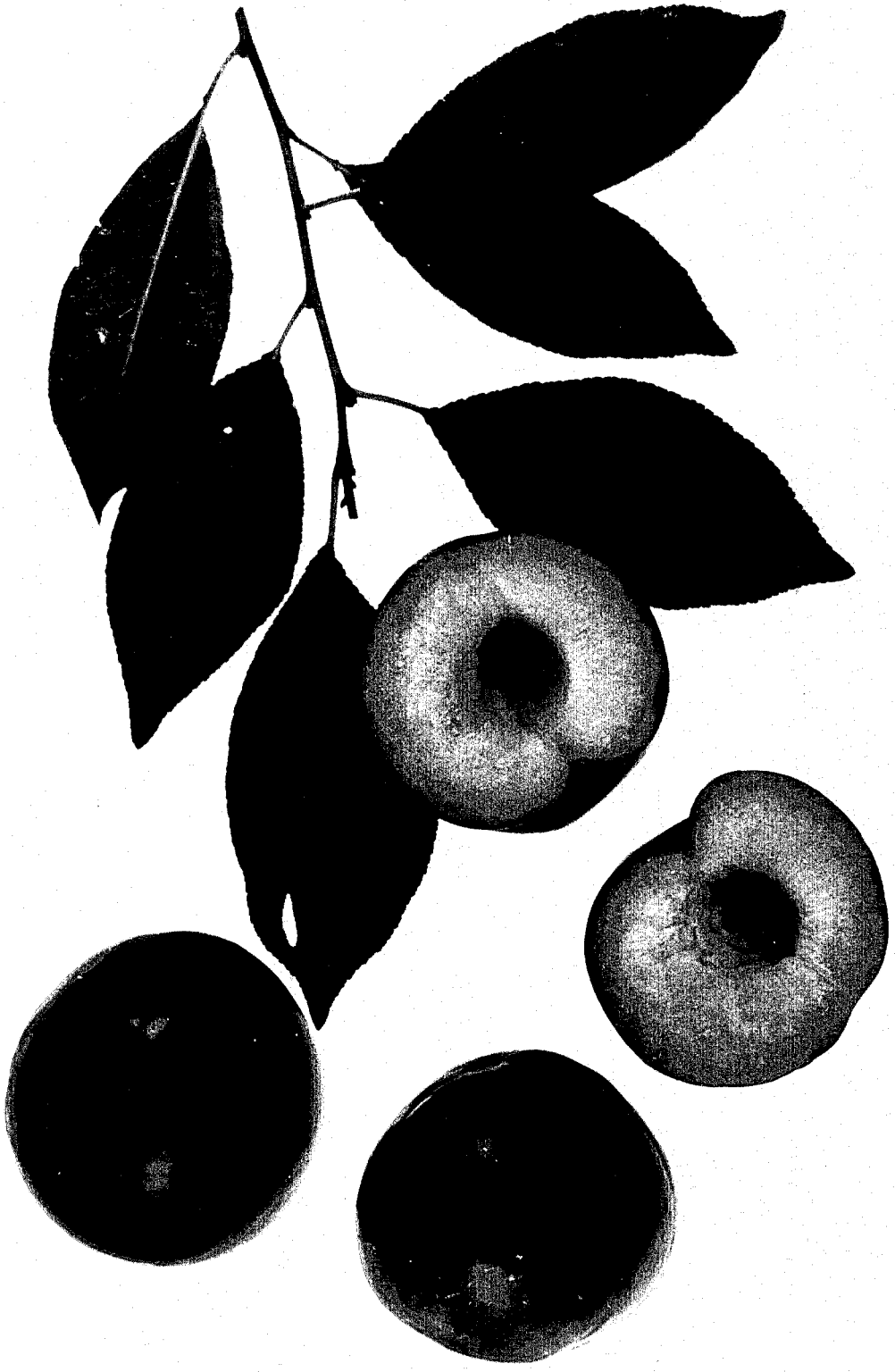

* * * * *